United States Patent [19]

Barcus et al.

[11] Patent Number: 5,049,235
[45] Date of Patent: Sep. 17, 1991

[54] POLY (METHYL VINYL ETHER-CO-MALEATE) AND POLYOL MODIFIED CELLULOSIC FIBER

[75] Inventors: Robert L. Barcus, Springfield Twp., Hamilton County; David W. Bjorkquist, Wyoming, both of Ohio

[73] Assignee: The Procter & Gamble Company, Cincinnati, Ohio

[21] Appl. No.: 458,011

[22] Filed: Dec. 28, 1989

[51] Int. Cl.$^5$ .................. D21C 9/00; D21H 11/20
[52] U.S. Cl. .................................. 162/9; 8/116.1; 162/123; 162/157.6; 427/212; 428/378; 604/376
[58] Field of Search ............... 8/116.1; 162/9, 157.6, 162/123; 604/376; 428/378; 427/212

[56] References Cited

U.S. PATENT DOCUMENTS

| | | | |
|---|---|---|---|
| 3,366,582 | 1/1968 | Adams et al. | 260/2.5 |
| 3,589,364 | 6/1971 | Dean et al. | 128/284 |
| 3,678,031 | 7/1972 | Schoggen | 260/231 |
| 3,759,861 | 9/1973 | Shimokawa | 260/31.4 |
| 3,858,585 | 1/1975 | Chatterjee | 128/290 |
| 3,889,678 | 6/1975 | Chatterjee et al. | 128/284 |
| 3,954,721 | 5/1976 | Gross | 526/14 |
| 3,989,586 | 11/1976 | Bashaw et al. | 162/168 |
| 4,018,951 | 4/1977 | Gross | 427/401 |
| 4,025,472 | 5/1977 | Lepoutre | 604/376 |
| 4,058,124 | 11/1977 | Yen et al. | 604/376 |
| 4,128,692 | 12/1978 | Reid | 428/378 |
| 4,151,130 | 4/1979 | Adams | 260/17.4 |
| 4,165,743 | 8/1979 | Denning | 128/290 |
| 4,210,489 | 7/1980 | Markofsky | 162/164 |
| 4,252,761 | 2/1981 | Schoggen et al. | 264/120 |
| 4,295,987 | 10/1981 | Parks | 252/194 |
| 4,354,901 | 10/1982 | Kopolow | 162/158 |
| 4,391,878 | 7/1983 | Drach . | |
| 4,552,618 | 11/1985 | Kopolow | 162/157.1 |
| 4,610,678 | 9/1986 | Weisman et al. | 604/368 |
| 4,654,039 | 3/1987 | Brandt et al. | 604/368 |
| 4,721,647 | 1/1988 | Nakanishi et al. | 428/283 |
| 4,743,244 | 5/1988 | Le Khac | 604/376 |
| 4,780,500 | 10/1988 | Sinka et al. | 524/559 |
| 4,888,238 | 12/1989 | Katz et al. | 428/378 |

FOREIGN PATENT DOCUMENTS

| | | |
|---|---|---|
| 1085810 | 9/1981 | Canada . |
| A192216 | 8/1986 | European Pat. Off. . |
| 50-5610 | 1/1975 | Japan . |
| 57-210100 | 12/1982 | Japan . |
| 61-132697 | 6/1986 | Japan . |
| 1540133 | 2/1979 | United Kingdom . |
| 1559716 | 1/1981 | United Kingdom . |

OTHER PUBLICATIONS

Gantrez AN Technical Data Sheet, GAF Corp.
Hebeish, Springer-Verlag, 1981; "The Chemistry and Technology of Cellulosic Copolymers".
Re. 32,649 Reissue of Brandt et al., supra.

Primary Examiner—Peter Chin
Attorney, Agent, or Firm—Rose Ann Dabek; Jerry J. Yetter; R. C. Witte

[57] ABSTRACT

Disclosed is a fiber comprising, chemically bonded together, (a) a conventional cellulosic fiber, such as a Kraft fiber or a chemithermomechanical pulp fiber; (b) poly(methyl vinyl ether-co-maleate) copolymer, such as the acid form of a 1:1 (molar) poly(methyl vinyl ether-co-maleate) copolymer, preferably having number average molecular weight of about 67,000-80,000; and (c) a polyol, such as polyethylene glycol; also disclosed are methods for making such fibers, especially evaporatively depositing an intimate mixture of the copolymer and polyol on the discrete fiber followed by thermally crosslinking at specific temperatures for limited periods; absorbent paper which can be made by wet-laying the fiber, especially in admixture with conventional fiber; and derivative paper structures, such as multi-ply disposable absorbent towels.

30 Claims, 1 Drawing Sheet

Fig. 1

POLY (METHYL VINYL ETHER-CO-MALEATE) AND POLYOL MODIFIED CELLULOSIC FIBER

FIELD OF THE INVENTION

This invention relates to fibers, such as Kraft fibers, which are chemically modified with certain poly(methyl vinyl ether-co-maleate) copolymers and polyols; to chemical methods for making such fibers; to improved paper which can be made by wet-laying the fibers, especially as a pulp in admixture with conventional papermaking pulps; and to derivative paper structures, such as multi-ply disposable absorbent towels.

BACKGROUND OF THE INVENTION

There is an ongoing interest in the development of absorbent articles such as paper towels. Disposable paper towels are widely used in the home for wiping spills, especially of water or watery liquids; for cleaning work-surfaces such as those of the kitchen and bathroom; for food preparation and handling; or for cleaning glass. More generally, absorbent papers are sometimes incorporated into other absorbent articles, such as dressings, catamenials and disposable diapers.

Manufacturing, more specifically sheet-forming, processes for paper are well-established in commerce. Papermaking machinery is very capital-intensive, and as a result, improvements in absorbent paper which do not require any major change in, or complication of, the paper-forming process tend to be highly appreciated. The processes of major importance include air-laying and wet-laying.

In outline, the latter process involves filtering a dilute dispersion of fibers onto a mesh (usually termed a Fourdrinier wire) and drying the resulting web. There is a large installed base of manufacturing equipment using continuous, high-speed machinery based on the wet-laying technique, representing considerable investment.

Conventional papermaking fibers suitable for wet-laying papermaking are cellulosic fibers which disperse well and can readily be filtered and dried. They typically absorb relatively small amounts of water, of the order of a few grams per gram of bone dry fiber.

The simplest notion for improving the absorbency of paper involves adding thereto a highly water-absorbent material, such as one of the gel-forming polycarboxylate polymers, which are well-known in the art. Very high absorbencies are possible, of the order of hundreds of grams of water per gram of polymer. Such materials have found particular utility as disposable diaper "superabsorbents".

Superabsorbents are however inherently very difficult to handle in a wet-laying process. Thus they tend to disintegrate under the relatively high shear forces involved in wet-laying papermaking. Moreover, they are difficult to filter, tending to block the Fourdrinier wire; and once deposited, they are very difficult to dry. The final product tends to be stiff and may not rewet to an acceptable degree when in use.

Applying the above-identified simple absorbency-improving notion to processes other than wet-laying has led to the development of a laminated structure or "sandwich" having outer plies of conventional paper and an inner layer consisting essentially of superabsorbent. However, the superabsorbent tends to leak out from the product paper structure, especially through pinholes or when the paper structure is torn. Slippery, gel-like material is released, which is a serious aesthetic disadvantage.

The deficiencies of the above approaches suggest a need to consider more than just the absolute magnitude of the absorbency which can be had from a particular paper additive. Thus, although absorbency is of primary importance, other requirements, such as ease of manufacture and product aesthetics, must be met. In addition, as distinct from water-absorbing capacity, another problem which has been identified in the context of absorbent structures has to do with rate of water uptake, in technical terms "wicking rate". Wicking rate is particularly important in a disposable paper towel which must quickly absorb a spill.

In principle, it is possible to suggest making absorbent paper by wet-laying an improved absorbent fiber (as distinct from particulate superabsorbents on one hand or conventional papermaking fibers on the other). Indeed, there are numerous literature reports of "absorbent fibers". However it would seem that these often involve mere physical coating of a fiber, such as processes involving precipitating absorbent polymers onto fibers or polymerizing monomers such as acrylic acid and methylenebisacrylamide in the presence of a fiber. In such situations, the chemical means are not present to covalently attach the polymer to the fiber. In consequence, the coating may not survive the shear forces involved in typical wet-laying operations, and may come off, the result being wire-blocking and/or drying problems similar to those mentioned above.

Grafted fibers are also well-known. Typical of grafted fibers are those made by graft copolymerizing methyl acrylate and cellulosic fibers in the presence of an appropriate catalyst such as cerium(IV) ammonium nitrate followed by hydrolyzing to the absorbent form. Absorbent grafted fibers are often not as strong as might be desired for wet-laying papermaking, since the low molecular weight monomer used in the preparation is capable of penetrating the fiber, polymerizing in the interior, so that when hydrolyzed and exposed to water, the fiber "balloons" internally and can easily shatter.

Various highly absorbent polymers have been extruded, and the extrudates have sometimes been termed "fibers". However, these materials are in fact not fibers in the usual sense of cellulosic papermaking fibers, rather they tend to be chemically homogeneous, and as with the common particulate superabsorbents, form slippery gels and encounter processing problems when wet-laid.

Oddly, to add to the above, there are reports in the literature of various chemicals apparently similar to those used herein apparently imparting wet-strength and/or hydrophobicity, i.e., water-resistance, to paper.

In view of the foregoing considerations, improvements in absorbent cellulosic fibers which do not make the fiber incompatible with wet-laying are highly desirable.

Accordingly, it is an object of the instant invention to provide a wet-layable papermaking fiber and pulp having an improved absorbent form.

More specifically, it is an object herein to provide a chemically modified fiber (hereinafter "the fiber of the invention") having three chemically bonded components, namely a cellulose of natural origin (such as an ordinary pulp fiber), a poly(methyl vinyl ether-co-maleate) copolymer and a polyol; which fiber has a water-absorbent chemical form (such as the sodium salt form), which is useful especially in that it is readily capable of being distributed into a web by wet-laying (e.g., as a pulp) in admixture with untreated fibers.

It is another object of the invention to provide absorbent wet-laid paper comprising the fiber of the invention.

A further object of the invention is the provision of a suitable process, unreliant on metal catalysts as used in common grafting processes of the art, for reproducibly making the fiber of the invention.

These and other objects are secured, as will be seen from the following disclosure.

BACKGROUND ART

For general discussion of coatings and chemical modifications of papermaking fibers and of paper see "Pulp and Paper, Chemistry and Chemical Technology", Ed. James P. Casey, Wiley-Interscience, 1981, Vols. I-IV. See also "Chemical Modification of Papermaking Fibers", K. Ward, Marcel Dekker, N.Y., 1973.

Japanese Laid-Open 50-5610, Jan. 21, 1975, discloses treating a preformed paper web with an aqueous solution containing polyvinylalcohol and various copolymers, especially maleic anhydride-methyl vinyl ether, followed by drying and thermally treating, to form high-wet-strength papers.

Papermaking wet-strength resins based on half-amides derived from maleic anhydride copolymers with various monomers are disclosed in U.S. Pat. No. 4,391,878, Drach, issued July 5, 1983.

Papermaking sizing agents and adhesives based on carboxylated vinyl polymers are disclosed in U.S. Pat. No. 3,759,861, Shimokawa, issued Sept. 18, 1973.

GANTREZ AN Technical Data Sheet, GAF Corp., suggests a number of useful applications for GANTREZ polymers in connection with papermaking. Notably, GANTREZ is suggested for use "as a beater additive to improve sizing, strength and dimensional stability." Further, "as a paper coating component, it can improve moisture. . . resistance."

U.S. Pat. No. 4,018,951, Gross, issued Apr. 19, 1977, discloses absorbent films prepared by heating methyl vinyl ether-maleate copolymers with crosslinking agents such as diglycidyl ethers or dihaloalkanes. The films can assertedly be used in absorbent articles.

U.S. Pat. No. 4,128,692, Reid, issued Dec. 5, 1978, discloses precipitating absorbent polymers onto fibers from an aqueous slurry.

U.S. Pat. No. 4,721,647, Nakanishi et al, issued Jan. 26, 1988, discloses an absorbent article comprising hydrophobic fibers and a water-absorbent polymer as spherical particles.

U.S. Pat. No. 4,295,987, Parks, issued Oct. 20, 1981, discloses a two-ply paper towel containing powdered absorbent copolymers. A layer can be sandwiched between two paper plies.

Brandt et al, U.S. Pat. No. 4,654,039, issued Mar. 31, 1987, reissued as Re 32,649 on Apr. 19, 1988, disclose superabsorbent polymers which can be used in absorbent structures.

Weisman, U.S. Pat. No. 4,610,678, issued Sept. 9, 1986, discloses air-laid absorbent structures comprising a mixture of hydrophilic fibers and discrete particles of a water-insoluble hydrogel.

Saotome, EP-A 192,216, published Aug. 27, 1986, discloses a water-absorbent fibrous structure, characterized as comprising a fibrous cellulosic material impregnated with a water-absorbent acrylic polymer and a fibrous material, which is produced by a method in which an aqueous solution of a monomeric component comprising acrylic acid and a radical initiator is diffused in a fibrous cellulosic material and heated, followed by blending with a fibrous material.

See also U.S. Pat. No. 4,354,901, Kopolow, issued Oct. 19, 1982 and U.S. Pat. No. 4,552,618, Kopolow, issued Nov. 12, 1985. The Kopolow disclosures relate to compression or heat treatment of boards in the dry state after a wet-laying papermaking process. The boards comprise "hydrocolloidal fibers" such as those of U.S. Pat. No. 3,889,678, Chatterjee et al, issued June 17, 1975.

Heat treatment of absorbent carboxyalkyl cellulose fibers in an absorbent structure to derive improved fluid absorptive properties is disclosed in U.S. Pat. No. 3,858,585, Chatterjee, issued Jan. 7, 1975.

Grafted, hydrolyzed absorbents are disclosed in "The Chemistry and Technology of Cellulosic Copolymers", Hebeish, Springer-Verlag, 1981; see also U.S. Pat. No. 3,366,582, Adams et al, issued Jan. 30, 1968 and U.S. Pat. No. 4,151,130, Adams, issued Apr. 24, 1979.

U.S. Pat. No. 4,252,761, Schoggen et al, issued Feb. 24, 1981, discloses sheets prepared from certain modified fibrous carboxymethylcellulose derivatives, sometimes known as bibulous cellulosic fibers. Such sheets are disclosed in patents including U.S. Pat. No. 3,678,031, Schoggen, issued July 18, 1972 and U.S. Pat. No. 3,589,364, Dean and Ferguson, issued June 29, 1971.

U.S. Pat. No. 4,780,500, Sinka et al, issued 25 Oct. 1988, discloses a coating composition for paper and paperboard containing pigment, binder, lubricant and water. The composition comprises a copolymer of 80%-98% (wt.) acrylic acid and 2%-20% (wt.) itaconic acid. The copolymer is water dispersible, has a molecular weight of 100,000-800,000 and is in acid, sodium, potassium and/or ammonium salt form. Included are compositions comprising by way of copolymer 95% (wt.) sodium acrylate and 5% (wt.) diammonium itaconate and having $M_w$ 250,000-400,000. Such copolymers can be used at a low level (0.05%-0.8% wt.) based on solids in the coating composition as a retention aid for the pigment and retard release of water from the coating composition without increasing its viscosity.

Patents relating to papermaking processes generally useful in the context of the present invention and incorporated herein by reference include U.S. Pat. No. 3,301,746, Sanford et al, issued Jan. 31, 1967; U.S. Pat. No. 3,905,863, Ayers, issued Sept. 16, 1975; U.S. Pat. No. 3,974,025, Ayers, issued Aug. 10, 1976; U.S. Pat. No. 3,994,771, Morgan, Jr. et al, issued Nov. 30, 1976; U.S. Pat. No. 4,191,609, Trokhan, issued Mar. 4, 1980; U.S. Pat. No. 4,300,981, Carstens, issued Nov. 17, 1981; U.S. Pat. No. 4,440,597, Wells et al, issued Apr. 3, 1984; U.S. Pat. No. 4,469,735, Trokhan, issued Sept. 4, 1984; and U.S. Pat. No. 4,637,859, Trokhan, issued Jan. 20, 1987.

SUMMARY

The present invention relates to a chemically modified fiber which has good absorbency properties. The fiber comprises, chemically bonded together, (a) a cellulosic fiber, very preferably a Kraft or chemithermomechanical fiber; (b) a poly(methyl vinyl ether-co-maleate) copolymer; and (c) a polyol, very preferably a polyethylene glycol.

In more detail, the invention encompasses a chemically modified fiber having a water absorbency and retention value in the range from about 15 g/g to about 100 g/g comprising, chemically bonded together: (a) a cellulosic fiber selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood (or hardwood) sulfite pulp fiber, unbleached softwood (or hardwood) sulfite pulp fiber, cotton linters, mercerized dissolving pulp fiber, unmercerized dissolving pulp fiber, and mixtures thereof; (b) a poly(methyl vinyl ether-co-maleate) 1:1 (this ratio being on a mole basis) copolymer having a number average molecular weight in the range from about 39,000 to about 80,000, and (c) a polyol, preferably a diol; wherein the proportion by weight of said poly(methyl vinyl ether-co-maleate) copolymer to said polyol is from about 250:1 to about 3:1 and the weight of said poly(methyl vinyl ether-co-maleate) copolymer plus said polyol per unit weight of said cellulosic fiber, (a), is in the range from about 0.3 to about 2, the poly(methyl vinyl ether-co-maleate) copolymer weight being expressed on an acid equivalent basis.

In the above, especially preferred polyols are selected from the group consisting of diols of formula $HO(CH_2CH_2O)_nH$ wherein n is from about 4 to about 154; and a preferred proportion by weight of poly(methyl vinyl ether-co-maleate) copolymer to said polyol is from about 30:1 to about 4:1.

In a highly preferred embodiment, the invention provides a chemically modified fiber wherein said poly(methyl vinyl ether-co-maleate) copolymer has number average molecular weight in the range from about 67,000 to about 80,000; n in said formula is from about 34 to about 100; and said weight of poly(methyl vinyl ether-co-maleate) copolymer plus polyol per unit weight of said cellulosic fiber, (a), is in the range from about 0.6 to about 1.5.

In other absorbent, quick-wicking chemically modified fiber embodiments, n in said formula is from about 70 to about 80; said proportion by weight of poly(methyl vinyl ether-co-maleate) copolymer to polyol is from about 10:1 to about 5:1; and said weight of poly(methyl vinyl ether-co-maleate) copolymer plus polyol per unit weight of cellulosic fiber, (a), is in the range from about 0.8 to about 1.2. Such fiber of the invention is especially useful when said water absorbency and retention value is in the range from about 50 g/g to about 80 g/g.

In the above-identified fiber of the invention, cations, which are inherently present in a charge-balancing amount, are generally selected from the group consisting of sodium, potassium, lithium, hydrogen and mixtures thereof, more preferably sodium, hydrogen and mixtures thereof.

A highly preferred form of the fiber of the invention for absorbency purposes is the sodium salt form, however the acid form is also useful, inter-alia because it can be taken to the absorbent sodium salt form by treatment with aqueous sodium hydroxide.

The invention encompasses papermaking pulps especially useful for wet-laying (although the same pulps are also useful in air-laying applications). Cellulosic papermaking pulps in accordance with the invention consist essentially of the above-identified fiber of the invention, or can be a mixture of that fiber with an unmodified fiber, such as the unmodified component (a) fiber identified supra. One such pulp consists essentially of : from about 5% to about 60% of the chemically modified fiber of the invention and from about 40% to about 95% of conventional cellulosic fiber (a).

Preferred chemically modified pulps in accordance with the invention are useful in the acid form, for example the pulp is largely acid-form when the content of cations which are hydrogen is such as to produce a pH of less than 5 when the pulp is dispersed in water. In this instance, the consistency can vary widely and the pulp can be shipped at high consistency since, as noted above, the chemically modified fiber is not absorbent.

The invention also encompasses the absorbent form of the cellulosic papermaking pulp, for example one comprising a major proportion of sodium-form fiber of the invention: typically, in such a pulp, the content of cations which are hydrogen is such as to produce a pH of from about 6 to about 9 when dispersed in water.

The fiber of the invention is a lightly crosslinked material. Particular attention is paid herein to adjusting the relative proportions of the starting-material components and to process conditions, so that a lightly crosslinked fiber can best be achieved.

Thus a preferred fiber of the invention can be secured by heating for specific curing times at particular curing temperatures a conventional cellulosic fiber onto which has been deposited an intimate mixture of the poly(methyl vinyl ether-co-maleate) copolymer and polyol. For proper control of the crosslinking, it is critical that the copolymer starting-material contain or be capable of forming maleic anhydride functionality during the thermal cure. In the case of the poly(methyl vinyl ether-co-maleate) copolymer, the 1,4-diacid functionality (present in the copolymer by virtue of maleate) will dehydrate during heating, to afford the requisite anhydride. Best results can be achieved by operating in specific, acidic pH ranges, and by control of the cation composition, especially by avoiding strongly coordinating polyvalent metal ions.

The term "fiber" is used to distinguish the immediate product of the invention from strong interbonded masses of paper fibers. The latter might seem similar based on a mere recital of ingredients, but do not have the dispersability and absorbency properties of the invention.

Thus, as noted, the fiber of the invention can be used on large scale as a papermaking pulp, especially in admixture with conventional papermaking fiber. Paper webs made by wet-laying such pulps are especially useful for making disposable absorbent paper towels having a unique distribution of absorbent material, which are capable of quickly absorbing appreciable amounts of water or watery fluids.

Useful embodiments of the invention include a wet-laid paper web, comprising at least 1% (preferably 5% to 10%) up to about 60% of chemically modified fiber of the invention. Excellent webs are secured when the content of the fiber of the invention is from about 20% to about 50%. The balance of such webs is typically conventional wet-laying papermaking fiber.

The invention also encompasses a disposable absorbent article, such as a disposable absorbent towel or a pad for a catamenial, comprising one or more plies of a wet-laid paper web as described herein.

The invention has several significant advantages. Thus the fiber of the invention leads to wet-laid absorbent paper free from aesthetic negatives in use, such as a tendency to shed particles of absorbent material or such as a tendency to feel slippery and gel-like when wetted. Other advantages include, but are not limited to, simplicity, nonreliance on expensive or toxic metal catalysts, the ability to improve the absorbency of "difficult" fibers such as chemithermomechanical pulp fibers (which is very desirable in view of the environmental advantages of such fibers as compared with chemical pulp fibers) and importantly, the ability to provide improved absorbent fibers which better accomodate the stresses of wet-laying papermaking with less tendency to disintegrate or cause wire-blocking or drying difficulties than conventional absorbent polymer-treated fibers.

All percentages herein are by weight and temperatures are ambient (25° C.), unless otherwise specifically noted.

DETAILED DESCRIPTION OF THE INVENTION

Chemical Structure Features-Description of the Drawing

A fiber in accordance with the instant invention is effectively a cellulosic fiber of natural origin to which is chemically attached a lightly crosslinked mixture of particular synthetic components, namely a poly(methyl vinyl ether-co-maleate) copolymer and a polyol. Without being limited by theory, the essential features of the chemical bonding occurring in a preferred embodiment of the invention are illustrated in FIG. 1.

Figure 1:
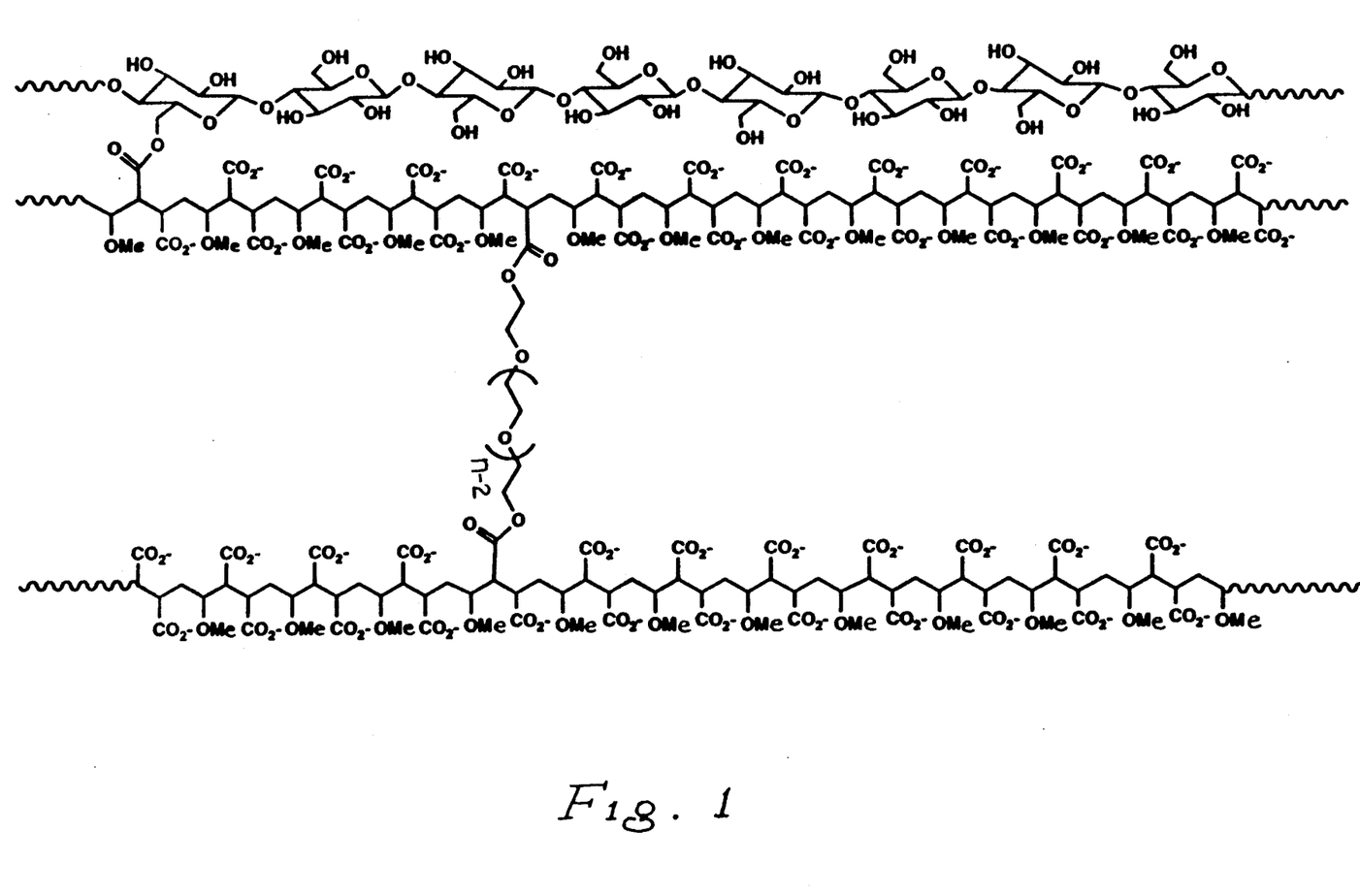
FIG. 1 illustrates the important types of chemical bonding between cellulose, maleate, methyl vinyl ether and polyethylene glycol in a fiber according to the invention.

FIG. 1 shows, covalently bonded together, (i) a cellulose moiety, (ii) maleate moieties of two kinds: those forming junctions between the other moieties (type 1) and those largely responsible for providing the carboxylate groups of the composition as a whole (type 2) (taken together, these are especially important for the absorbent properties of the fiber of the invention), (iii) methyl vinyl ether moieties and (iv) a polyol moiety, which in FIG. 1 is one derived from a polyethylene glycol. Not shown are the fiber as a whole, of which the depicted cellulose moiety is but a part, as well as cations (sodium being preferred), which are inherently present in a charge-balancing amount and are primarily associated with the negative charges of the copolymer; water molecules; and any imperfections, such as incompletely reacted moieties.

Another feature of the invention illustrated in FIG. 1 is that the relative proportion of maleate (type 1) to maleate (type 2) is low, ensuring a relatively light crosslinking. Moreover, the lightly crosslinked methyl vinyl ether/maleate/polyol structure is chemically attached to the cellulosic fiber.

The fibers of the invention are quite different from grafted cellulosic fibers of well-known kinds which can be made, for example by cerium-catalyzed polymerization of methyl acrylate in presence of a cellulosic fiber followed by sodium hydroxide hydrolysis. A known technique for finding the location of a highly charged synthetic polycarboxylate polymer in relation to a material such as cellulose which is less highly charged involves mapping the distribution of charge-balancing cations, such as sodium, by X-ray Energy Dispersive Spectroscopy. Sodium ion maps of preferred fibers of the invention show substantially intact cellulose regions without high concentrations of sodium being present between the fiber wall and the fiber lumen, whereas there is a significant proportion of sodium distributed between the fiber wall and the lumen in typical hydrolyzed methyl-acrylate grafted fibers.

Without being bound by theory, it is believed that having a fiber with substantially intact cellulosic regions of natural origin and a chemically attached, lightly crosslinked, water-swellable poly(methyl vinyl ether-co-maleate) copolymer are important for securing the benefits of the instant invention.

Composition of fiber of the invention

In general, the fiber of the invention comprises, chemically bonded together: (a) a cellulosic fiber; (b) a poly(methyl vinyl ether-co-maleate) copolymer and (c) a polyol.

(a) Cellulosic Fiber.

The cellulosic fiber, to which the remaining components are bonded in the fiber of the invention, is a conventional material such as a Kraft or sulfite pulp fiber. In general, it is selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood sulfite pulp fiber, bleached hardwood sulfite pulp fiber, unbleached softwood sulfite pulp fiber, unbleached hardwood sulfite pulp fiber, cotton linters, mercerized dissolving pulp fiber, unmercerized dissolving pulp fiber, and mixtures thereof.

Preferred cellulosic fiber is selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, and mixtures thereof.

Highly preferred embodiments of the invention include those made from chemithermomechanical pulp fiber and bleached Kraft fiber such as southern softwood Kraft fiber. As illustrated hereinafter, there may be somewhat different preferred synthesis conditions, especially relating to pH, curing temperature and curing time, depending on which of these highly preferred fibers is chosen.

Preferably, such fiber will be of a quality deemed good or superior for the purposes of conventionally making wet-laid paper webs. More specifically, fiber having relatively low levels of "fines" and a good staple length are preferred.

(b) Poly(methyl vinyl ether-co-maleate) Copolymer.

The fiber of the invention also contains a poly(methyl vinyl ether-co-maleate) copolymer. In general, this copolymer is a 1:1 copolymer. That is to say, the methyl vinyl ether content is about 50 mole % and the maleate content is about 50 mole %. The copolymer can be further characterized as an "alternating" copolymer.

The poly(methyl vinyl ether-co-maleate) copolymers useful herein are selected members of a known class of copolymers. They may be prepared by conventional, art-known techniques for copolymerizing methyl vinyl ether and maleic anhydride. The copolymer is commercially available from GAF Corp. (GANTREZ, CAS 9011-16-9); as well as from other suppliers. The anhydride forms of the copolymers are further illustrated by GANTREZ AN-119, GANTREZ AN-139, GANTREZ AN-149, GANTREZ AN-169, and GANTREZ AN-179. These copolymers have number average molecular weights, $M_n$, of 20,000, 41,000, 50,000, 67,000 and 80,000, respectively, as identified by GAF Corp. The corresponding acid forms can be seciured by simple hydrolysis. Alternatively, GANTREZ S-97, a maleic acid form of the copolymer, can be purchased either as a solid or in an aqueous solution.

Selection of a copolymer useful herein is based on a recognition that any given maleate moiety in the copolymer will be unreactive for the purposes of forming the fiber of the invention if at the time thermal crosslinking is attempted, maleic anhydride moieties are not either already present or cannot be formed. Such resistance to forming the anhydride is exhibited especially when the maleate component of the copolymer is completely neutralized, such as in the form of the diammonium salt, and to an even greater extent, when the maleate component of the copolymer is co-ordinated with multivalent metal ions such as those of calcium, magnesium or iron. For practical purposes, it is therefore highly preferred both to use the acid (or anhydride) form of the copolymer and, at the same time, to limit the content of multivalent metal cations in the copolymer.

In accordance with the above-illustrated embodiments, copolymers useful herein have nominal number average molecular weight, (as identified by GAF Corp.) in the general range from about 39,000 to about 80,000, more preferably about 41,000 to about 80,000, most preferably 67,000 to about 80,000. (The corresponding weight average molecular weights of the preferred materials for use herein are of the order of several hundred thousand, or higher). Within practical limits, the absorbent properties of the fiber of the invention increase significantly as molecular weight of the copolymer increases. Without being limited by theory, it is believed that even higher copolymer molecular weights than those illustrated herein may be useful. Molecular weights below the specified lower limits are believed to be inconsistent with securing the absorbency benefits of the invention.

As found in the fiber of the invention, the copolymer is chemically bonded to the cellulosic fiber and to the polyol.

(c) Polyol

The polyol component of the fiber of the invention is an alcohol having two or more —OH groups. In the fiber of the invention, as illustrated in FIG. 1 the polyol is at least partially chemically incorporated by reaction with maleic anhydride moieties of the copolymer (see the chemistry of the synthesis further discussed hereinafter) so that it is no longer in the free state and acts as a crosslinking group in the fiber of the invention. Although a wide variety of polyols are useful herein, preferred polyols are diols, especially water-soluble diols. Although any polyol consisting essentially of C, H and O can be used, the polyol is typically selected from the group consisting of polyethylene glycol, polyvinyl alcohol, ethylene glycol, propylene glycol, glycerin, pentaerythritol and the like.

In preferred embodiments, the polyol is a diol such as polyethylene glycol, and can have varying molecular weight. Suitable diol materials have the formula $HO(CH_2CH_2O)_nH$ wherein n is from about 4 to about 154, more preferably from about 34 to about 100, most preferably from about 70 to about 80. Preferred embodiments of these materials are to be found in the commercial PEG 200–7000 series. Thus, commercial PEG 200 corresponds with n in the above formula of about 4, PEG 1000 corresponds with n of about 22, PEG 1500 corresponds with n of about 34, PEG 3350 corresponds with n of about 76 and PEG 6800 corresponds with n of about 154. In practice, it is found that although quickwicking fiber of the invention can be prepared with PEG 200, absorbency results are optimal with PEG 3350.

Proportions of components

In general, the proportion by weight of poly(methyl vinyl ether-co-maleate) copolymer to polyol in the fiber of the invention is in the range from about 250:1 to about 3:1, more preferably from about 30:1 to about 4:1, most preferably from about 10:1 to about 5:1. When the polyol has a low molecular weight, such as ethylene glycol, the weight amount of polyol is relatively low. As the molecular weight increases in a homologous series, such as in PEG of progressively increasing molecular weight, the relative weight of polyol increases. When the polyol has many —OH groups, as in polyvinylalcohols, the relative proportion by weight of polyol may be low, even though the molecular weight of the polyol is high.

Without being limited by theory, it is believed that the proportion of copolymer to polyol is very important for controlling the crosslink density in the fiber of the invention. The above-recited ranges take into account that maintaining a relatively constant, consistently low crosslink density is preferred.

In the fiber of the invention, the add-on, that is to say the weight of poly(methyl vinyl ether-co-maleate) copolymer plus polyol ((b) plus (c)) per unit weight cellulosic fiber (a) is in the general range from about 0.3 grams per gram to about 2 grams per gram, more preferably from about 0.6 grams per gram to about 1.5 grams per gram, most preferably from about 0.8 to about 1.2 grams per gram. It should be appreciated that as the add-on is progressively decreased, the absorbency of the fiber decreases but the fiber may become somewhat easier to process. On the other hand, excessive add-on, outside the scope of this invention, can lead to an appreciable content of pieces of absorbent polymer which are not chemically attached to the fiber. Moreover, there appears to be a plateau effect of absorbency performance and usefulness when much more than the stated upper limit of add-on is used.

It should be appreciated that add-on levels herein are, in percentage terms, rather high, i.e., 30% to 200%. These levels are very much higher than in conventional paper coatings, wet-strength additive applications or the like.

The poly(methyl vinyl ether-co-maleate) copolymer weight referred to hereinabove and throughout the specification is by convention expressed on an acid equivalent basis. That is to say, regardless of the form of the poly(methyl vinyl ether-co-maleate) copolymer used in the synthesis of the fiber of the invention, and equally regardless of the form of the product fiber, the convention is adopted of everywhere specifying the poly(methyl vinyl ether-co-maleate) copolymer weight as though it were in the maleic acid form. In this manner, regardless of the weight of cations which may be present, the relative proportion of poly(methyl vinyl ether-co-maleate) copolymer to the cellulose and polyol components is unambiguously determined.

Cations

Since the fiber of the invention contains negatively charged carboxylate groups, especially those associated with the poly(methyl vinyl ether-co-maleate) copolymer, cations will inherently be present therein in a charge-balancing amount.

In the fiber of the invention, the cations are generally selected from sodium, potassium, lithium, hydrogen and mixtures thereof, more preferably sodium, potassium, hydrogen and mixtures thereof, most preferably sodium, hydrogen and mixtures thereof.

When not in the anhydride form, a similar range of cation composition applies to the copolymer starting-material, however the most highly preferred cation for the starting-material copolymer, if any is present, is hydrogen. Thus the starting form of the copolymer is most preferably the acid or anhydride form.

The fiber of the invention can be in the acid form, in which it is not directly useful as an absorbent but is very useful for long-term storage or shipping from the fiber manufacturing plant to the papermaking plant at high consistency; or it can be in the highly absorbent sodium form. Other such water-soluble monovalent cation salts of the fiber of the invention, such as the potassium salt, as noted, are likewise useful absorbents.

Importantly, polyvalent cations such as those of iron, calcium, magnesium and aluminum are avoided, both in the starting copolymer and in the fiber of the invention, as much as practical considerations will allow. Such cations can not only interfere with the synthesis of the fiber but also with the absorbent properties of the product fiber.

Absorbency property

The fiber of the invention is most useful as an absorbent material. Thus, it has a water absorbency and retention value (WAARV)—this quantity being measured according to the procedure given in "Test Methods" hereinafter—in the range from about 15 g/g to about 100 g/g, more preferably from about 25 g/g to about 90 g/g, most preferably from about 50 g/g to about 80 g/g.

The term "retention" in WAARV takes into consideration that the test method involves centrifugation, so that water quite tenaciously retained by fiber, pulp or paper is included in the absorbency measurement. Moreover, WAARV values are measured at a constant alkaline pH so that values are reproducible and can be compared. WAARV can be used to characterize both acid-form and salt-form fibers according to the invention because during the test, in-situ conversion of acid-form to salt-form fiber takes place. Moreover, WAARV can be used to measure the absorbency of wet-laid webs comprising the fiber of the invention.

Without being bound by theory, it is believed to be important that the fiber herein is substantially discrete rather than a mass of strongly interbonded fibers with significant amounts of polymer located at the fiber crossovers. That latter behavior, believed inferior for absorbency purposes, is the kind to be expected when the fiber results from (i) forming paper, e.g., on a Fourdrinier wire then (ii) applying a polymer, for example by spray-on or impregnation, then (iii) crosslinking the polymer: such a sequence, or the resulting product, are not in accordance with this invention.

Thus the fiber of the instant invention results from (i) concentrating the polymer components as much as possible on individual cellulosic fibers prior to making paper, then (ii) thermally crosslinking to form the chemical bonds between the polyol-copolymer mixture and the fiber. The resulting fiber can then (iii) be used in bulk as a papermaking pulp or furnish for wet-laying to achieve an absorbent, quick-wicking paper web free from aesthetic disadvantages.

Chemistry of Synthesis

It should be understood that water ($H_2O$) is eliminated in the chemical reactions of curing or thermally crosslinking which are normally used to form the fiber of the invention. Without being limited by theory, the following chemical reactions are believed to occur:

(I) part of the maleate moieties of the copolymer dehydrate in the presence of heat to give maleic anhydride moieties;

(II) a portion of the maleic anhydride moieties further react by acylating the —OH groups of the starting-material cellulosic fiber: this results in at least partial chemical attachment of copolymer to fiber via covalent ester bonds of cellulose to maleate; and (III) a portion of the maleic anhydride moieties further react by acylating the —OH groups of the polyol: since the polyol is at least difunctional, this results in crosslinking of the copolymer and polyol; and (IV) indispensably for the purposes of the invention, there is a large excess of maleate and/or maleic anhydride moieties, which all ultimately rehydrate when the cured fiber is exposed to water, forming carboxylate groups.

To be noted is that the terms "curing", "thermally crosslinking", "crosslinking" and "chemically reacting" are equivalent herein, at least inasmuch as they refer more or less specifically to producing the fiber of the invention. Curing temperatures and times are very important and are discussed at length hereinafter.

Preparation of fiber of the invention

In general, fiber of the invention can be made by lightly crosslinking, typically by a thermal method, a cellulosic fiber of a quality suitable for wet-laying papermaking, typically a conventional wet-laying papermaking fiber such as bleached southern softwood Kraft or chemithermomechanical fiber, with an intimate mixture of poly(methyl vinyl ether-co-maleate) copolymer and polyol.

It is essential that immediately prior to thermal crosslinking, the poly(methyl vinyl ether-co-maleate) copolymer should be capable of producing an acidic solution in water, for the simple reason that the fully neutralized salts, such as the diammonium salt, the disodium salt etc., are incapable of thermally eliminating water and of forming maleic anhydride moieties, which, as discussed supra, is an essential part of the chemical reaction leading to the fiber of the invention.

It is consistent with the sense of the invention to deposit copolymer-polyol mixtures on cellulosic fibers using a process such as extrusion, evaporative deposition or any similar deposition method, regardless of whether it involves a fluid medium or carrier or not.

When there is no medium to be removed, the mixed fiber-copolymer-polyol can be directly crosslinked by heating at suitable curing temperatures for limited curing times, provided that an intimate mixture of copolymer and polyol has been formed.

When it is desired to make fibers without resorting to expensive process equipment, a medium can be used to deposit the poly(methyl vinyl ether-co-maleate) copolymer on the starting-material cellulosic fiber. In this event, the medium should preferably be capable of substantially completely dissolving the poly(methyl vinyl ether-co-maleate) copolymer and the polyol, so that an intimate mixture of the two can be evaporatively deposited on the cellulosic fiber. The medium should be capable of substantially complete evaporation at normal or reduced pressures below the temperatures at which thermal crosslinking occurs. Acetone, acetone/water mixtures, acetone/water/methanol mixtures, and methanol/water mixtures are all quite suitable, as as are water mixtures with other common low-boiling water-miscible organic solvents, but water alone is highly preferred, especially on account of low cost and low toxicity.

When water dissolves the poly(methyl vinyl ether-co-maleate) copolymer and polyol, the result is an "aqueous medium" for the purposes of this invention. Typically, the aqueous medium has a percentage by weight of poly(methyl vinyl ether-co-maleate) copolymer plus polyol which is about 10% by weight or higher, more preferably the concentration is about 20%. Much more importantly, the aqueous medium is found to behave quite differently, in terms of its suitability, depending on the pH. In general, the pH of the aqueous medium must lie in the range from about 1.6 to about 3.5, more preferably from about 2.5 to about 3.0. When the cellulosic fiber to be treated is chemithermomechanical fiber, the entirety of the above-recited pH range of from about 1.6 to about 3.5 gives acceptable results but the range from about 1.6 to about 3.0 is preferred. When other cellulosic fiber types are being treated, the pH of the aqueous medium should very preferably be in the somewhat narrower range from about 2.5 to about 3.5. Below the above-specified pH minima, depending on the precise type of cellulosic fiber, the cellulosic fiber will tend to degrade. Moreover, at pH values much above the stated upper limit, the degree of crosslinking in the crosslinking step is sharply reduced, to an unacceptable extent.

Water used to make the aqueous medium is preferably substantially free from polyvalent cations such as those of calcium, magnesium, iron and aluminum. In any event, the content of such cations should not be so high as to inhibit the thermal crosslinking reaction.

Once the poly(methyl vinyl ether-co-maleate) copolymer and polyol are dissolved and an aqueous medium is formed, the medium can be applied to cellulosic fibers in whatever manner desired, provided that these fibers are discrete or dispersed rather than knit together in the form of a bonded web.

The mixture of cellulosic fibers and aqueous medium is evaporated at non-crosslinking temperatures. For practical purposes, such temperatures are generally below about 75° C., typically in the range 50° C. to 70° C. At higher temperatures, there is an increased risk of uncontrolled crosslinking. Lower temperatures can be used: for example water can be evaporated by freeze-drying.

Evaporation of water results in a substantially dry, intimate mixture of the poly(methyl vinyl ether-co-maleate) copolymer and polyol on the cellulosic fibers.

Preferably, the evaporation is carried out under conditions which avoid sticking together of the fibers. One suitable approach believed to be good for removing water from the aqueous medium and uniformly depositing the poly(methyl vinyl ether-co-maleate) and polyol as an intimate mixture on the cellulosic fiber surface involves the use of a supercritical fluid such as supercritical carbon dioxide for extracting the water.

A preferred approach to the depositing operation which has been found quite satisfactory, especially on grounds of economy and simplicity, is to evaporate a thin layer of the poly(methyl vinyl ether-co-maleate) copolymer/polyol/fiber/water mixture. Although there may be some sticking together of fibers, the evaporated layer is readily repulped (after the crosslinking step described in detail below) to give substantially discrete fibers of the invention.

In general, crosslinking or "curing" herein involves applying a controlled amount of heat, which can be achieved under a range of temperatures and times.

Thus, in a preferred embodiment, the invention encompasses a process for preparing a chemically modified fiber having a water absorbency and retention value in the above-recited ranges, comprising a step of: thermally crosslinking, at a curing temperature of from about 100° C. to about 140° C., more preferably from about 110° C. to about 135° C. for a curing time of from about 120 minutes to about 3 minutes, more preferably from about 45 minutes to about 4 minutes, a starting-material pulp consisting essentially of the above-identified cellulosic fiber (component (a)); with an intimate mixture of poly(methyl vinyl ether-co-maleate) copolymer (above-identified as (b)), and a polyol (component (c) identified hereinabove); wherein the proportion by weight of poly(methyl vinyl ether-co-maleate) copolymer to polyol is in the above-recited general ranges and the weight of poly(methyl vinyl ether-co-maleate) copolymer plus polyol per unit weight of cellulosic fiber, (a), is likewise as recited hereinabove.

In practice, the copolymer-polyol-treated dry cellulosic fibers are preferably exposed to heat as a thin layer. Preferably, a pre-heated oven is used for best control of the crosslinking or curing reaction. In order to minimize curing time at any given curing temperature, the practitioner will preferably use a flow of hot air and will permit access of the hot air to both sides of the fiber layer by first removing any substrate which may have been used in the above-described fiber-polymer contacting procedures: in practice, this is most easily accomplished when the substrate is "non-stick", for example, polytetrafluoroethylene (PTFE). Aluminum foil can also be used with satisfactory results.

Based on this appreciation of the curing operation, the practitioner will readily recognize that it is possible to conduct evaporative deposition and thermal crosslinking, indeed the entire synthesis of the fiber of the invention, in a continuous or semi-continuous mode. For example, a PTFE carrier belt can carry the cellulosic fiber, copolymer and polyol through the evaporative deposition stage and into the curing stage in the synthesis process.

It has however been found that it is preferred to cure in the absence of a substrate (for improved access of hot air to both sides of the fibrous layer) or in the presence of a substrate which does not overly affect heat flow into the above-described thin layer during curing.

In the above and throughout the specification, curing times are defined as the total period of exposure to hot air at the curing temperature, the fiber layer being introduced to the hot air oven at ambient temperature.

The practitioner should be aware that for best results, especially when manufacturing on a large scale, it is advisable to optimize the curing temperature and time at the scale chosen, by the simple expedient of measuring Fiber Yield and Water Absorbency and Retention Value of the fiber of the invention, each as defined in "Test Methods" hereinafter, over a series of curing temperatures and times in accordance with the invention.

When curing is complete, the fiber of the invention (where necessary, it is termed "raw" fiber elsewhere herein to distinguish the fiber at this juncture from the absorbent, salt-form ultimately produced) is repulped, preferably with an amount of shear which will not significantly reduce the staple. Repulping is generally carried out in water under acid conditions, typically at a pH of about 2 to about 4, more preferably at pH of about 2 to about 3 (hence the term "acid repulping" can be used to characterize this step). In the acid repulping step, the fiber of the invention is substantially in the acid form. In this form, the fiber is non-swollen and is readily manipulated, thus in this form it has the advantage that it can conveniently be shipped as a concentrated slurry from the fiber manufacturing plant to the papermaking plant if desired.

After repulping, the fiber of the invention can be secured substantially in the dry, sodium-salt form by a fiber-swelling step. The fiber-swelling step simply involves neutralizing with sodium hydroxide, preferably to a pH of from about 7.5 to about 9, whereon the fiber swells greatly. The fiber-swelling step can be quite slow, and may take up to 1-2 days. It is a curious feature of the fiber of the invention that the first conversion from the acid form to the sodium salt form is of such duration, since subsequent interconversions between the acid and salt forms can be carried out quite rapidly by adding acid or base, as needed.

If desired, after the fiber-swelling step, the fiber of the invention can be filtered and dried, typically at temperatures of about 80° C.-90° C., although this is not necessary and is not usually practiced if the fibers are to be used as a pulp for wet-laying papermaking.

To be noted is that fibers of the invention in the sodium salt form are superior in their heat resistance as compared with the corresponding fibers in the acid form. If in the above, the sodium hydroxide is substituted by potassium hydroxide or lithium hydroxide, the corresponding potassium and lithium salt forms of the fiber of the invention can be secured.

For the practical reason that the fiber of the invention is typically used in a wet-laying process, the practitioner generally does need to dry the salt form of the fiber prior to use in wet-laying, but can directly use it as a slurry.

As noted supra, it is possible to use solvents other than water for preparing the fiber of the invention. Thus, in alternate process embodiments, the aqueous medium can be replaced by acetone/water mixtures or even by acetone alone, provided that the polyol dissolves. In such embodiments, the anhydride form of the copolymer starting material (b), i.e., poly(methyl vinyl ether-co-maleic anhydride), is generally used. In this form, the copolymer is quite soluble in acetone. When some water is needed to assist dissolving the polyol, very low relative proportions of water to acetone, such as about 1 ml of water per 380 ml of undried reagent grade acetone, are typically sufficient. Evaporative deposition of polyol and copolymer on the fiber can then be carried out by distillation at atmospheric pressure or, alternately, at reduced pressure, e.g., by means of a rotary evaporator. This results in the deposition of an intimate mixture of the copolymer (b) and polyol (c) onto the starting-material cellulosic fiber (a) (the latter maintains a substantially discrete or "loose" state). The curing step (as described supra) is then carried out. If desired, curing may be carried out directly in the flask used for the evaporative deposition.

When the anhydride form of the copolymer and a medium with low water content are used to make the fiber of the invention, the fiber which is produced in the curing step contains relatively few maleate moieties and appears even more hydrophobic than is usually the case for the acid-form fiber of the invention. Without being bound by theory, this is believed to be due to the relatively high level of residual maleic anhydride moieties. Accordingly, when a low water-content medium has been used, the work-up to produce the absorbent sodium-salt form of the fiber typically requires an additional hydrolysis step which is positioned prior to the repulping step. Thus, after curing, the high-anhydride containing fiber is preferably subjected to a period of hydrolysis with acid or base before continuing with acid repulping and fiber-swelling steps. During the hydrolysis, anhydride moieties react to form maleate: the acid repulping and fiber swelling steps then carried out result, as usual, in the absorbent, sodium salt form of the fiber of the invention.

Webs and Wet-Laying Processes for their Production

In other embodiments, the invention provides a wet-laid paper web comprising from about 5% to about 60%, more preferably from about 10% to about 60%, most preferably from about 20% to about 50% of the fiber of the invention (or equivalently, the product of the above-identified synthesis process). The balance of the composition can be conventional papermaking fibers, such as fibers having an identical composition to the starting-material fibers. When mixtures of fiber of the invention and conventional papermaking fibers are co-distributed in a wet-laid web, highly absorbent, quick-wicking structures result.

Preferred papermaking processes useful herein, as incorporated by reference in the background art discussion hereinabove, include continuous wet-laying processes designed for making conventional highly absorbent paper.

A feature of interest which distinguishes several such processes and is believed to be useful in the context of the present invention is to avoid compressing or squeezing (e.g., calendering) the wet-laid web as much as possible during drying: also, it can be helpful to dry the webs containing the fiber of the invention using blow-through air dryers of conventional construction. This produces a rather open, absorbent web.

A modification of a conventional wet-laying process which is especially helpful for making wet-laid webs according to the present invention in a continuous operation simply involves wet-laying at acidic pH, typically in the range from about 3 to about 5, followed by partially drying the wet-laid web, neutralizing on-line with a sprayed-on sodium carbonate or potassium carbonate solution (sodium hydroxide may be used but can yellow the web if not carefully applied), and drying, especially with the aid of a conventional Yankee dryer.

Disposable absorbent towels

The wet-laid webs can be used as plies in a two-ply or multi-ply disposable absorbent structure such as a disposable absorbent towel. All that needs to be done to secure such disposable absorbent structures is to combine plies comprising at least one wet-laid paper web according to the invention, in a conventional converting operation, e.g., simple glueing or bonding of the plies together.

Alternate embodiments of the invention

The fiber of the invention is not limited to use as an absorbent for disposable absorbent towels, but may be used for making catamenial pads, absorbent dressings, pantiliners and the like.

Fibers in accordance with the invention are further illustrated by the following Examples.

Experimental

Starting-materials

Poly(methyl vinyl ether-co-maleate) copolymers are obtained from GAF Chemicals Corp., Wayne, N.J. Suitable anhydride forms of the copolymers are GANTREZ AN-149, GANTREZ AN-169, and GANTREZ AN-179, having number average molecular weights, $M_n$, of 50,000, 7,000 and 80,000, respectively, as identified by GAF. The corresponding acid forms can be obtained by aqueous hydrolysis. A suitable acid-form copolymer directly obtainable commercially from the same supplier is GANTREZ S-97. It can be purchased either as a solid or as an aqueous solution.

Polyethylene glycols (these preferred polyols are commonly known as "PEG", various suppliers being suitable) as used in the Examples have nominal molecular weights of 200, 1000, 1500, 3350, and 6800. PEG 200 is obtained from Polysciences Inc., Warrington, Pa. PEG 1000, PEG 1500 and PEG 6800 are obtained from Scientific Polymer Products, Inc., Ontario, NY. PEG 3350 is obtained from Sigma Chemical Co., St. Louis, MO.

Southern softwood Kraft (SSK) pulp and northern softwood Kraft (NSK), bleached hardwood aspen pulp, bleached hardwood sulfite pulp, cotton linters, bleached hardwood eucalyptus pulp, dissolving SSK (V-60), and mercerized dissolving SSK (V-5), are obtained from P&G Cellulose, Memphis, Tenn. Chemithermomechanical pulp is obtained from Quesnel Paper Co., Quesnel, British Columbia, Canada.

Unless otherwise noted, acetone is reagent grade and water is triply distilled.

EXAMPLE I

Preparation of fiber of the invention.

GANTREZ S-97 (3.35 g) is dissolved by adding it portionwise to 30 ml of water which has been acidified to pH 2.00 with 1 Molar hydrochloric acid while stirring and heating to 65–70° C. To the solution is added polyethylene glycol (0.500 g, nominal molecular weight 3350). Stirring is continued until dissolution is complete. The resulting aqueous medium is now cooled to ambient temperature. The pH of this medium (the "pH of the aqueous medium" referred to elsewhere herein) is measured to be 1.60. Loose fibers of chemithermomechanical pulp (3.00 g) are added. The resulting slurry is thoroughly mixed and is spread out into a thin layer on a piece of aluminum foil. The slurry layer is dried in an oven at 65–70° C., a temperature selected to minimize or avoid crosslinking reactions. The layer, now about 1 mm thick, is removed from the foil and is cured by placing it in an oven preheated to a curing temperature of 130° C. The curing time is 6.5 minutes. The layer is cooled to ambient temperature. This yields raw fiber in the acid form, which is not particularly absorbent. The fiber is then repulped. In practice it is convenient to break it into small pieces and add it to 500 ml of distilled water. After further stirring (e.g., 1 hour) the pH of the mixture is adjusted to 2.0 with hydrochloric acid and it is mixed in a Waring Blendor for 1 minute on low speed. The fibers, still in the acid form, are collected by suction filtration in a Buchner funnel fitted with a handsheet forming wire, are washed with 500 ml of water, and are re-suspended into 500 ml of water. The slurry pH is adjusted to 8.5 using 1 Molar sodium hydroxide in water. (Using potassium hydroxide or lithium hydroxide instead of sodium hydroxide at this stage would result in the potassium or lithium form of the fibers.) Over one day, the pH is periodically checked and readjusted to 8.5 with sodium hydroxide. During this period, the fibers exchange to the sodium salt form, which is highly absorbent. Thus, the fibers swell up. The fully swollen fibers of the invention are collected by suction filtration and are washed with distilled water. Their wet weight is 285 g and their consistency (Test Method given hereinafter) is determined to be 2.10 %, from which the Fiber Yield (Test Method given hereinafter) is calculated to be 5.99 g of fiber of the invention. The Conversion (Test Method given hereinafter) is calculated as about 87 %. The WAARV of the fiber of this Example (Test Method given hereinafter) is determined as 40.4 g/g.

EXAMPLE II

Preparation of fiber of the invention.

Chemithermomechanical pulp (3.00 g) is repulped in 300 ml of acetone in a Waring Blendor on low speed for 1 minute. The resulting slurry is transferred into a 1 liter round-bottom flask. To this slurry is added a solution of GANTREZ AN-169 (3.00 g) dissolved in 75 ml of acetone. Polyethylene glycol (0.500 g, nominal molecular weight 3350) is dissolved in a mixture of acetone (10 ml) and water (about 0.5–1.0 ml) and added to the slurry. The mixture is stirred for about three hours and then the solvent is evaporated in vacuo. The fibers are then cured by placing the flask into an oven preheated to 130° C. The curing time is 6.5 minutes. After cooling to ambient temperature, 600 ml of water which has been adjusted to pH 11.0 with 1 Molar sodium hydroxide is added and the mixture is allowed to stir overnight. The fiber is then repulped. In practice, it is convenient to adjust the pH of the mixture to 2.0 with 1 Molar hydrochloric acid and then it is mixed in a Waring Blendor on low speed for 1 minute. The fibers are collected by suction filtration in a Buchner funnel fitted with a handsheet forming wire and washed with 400 ml of water. The fibers in the acidic form, which are not particularly absorbent, are re-suspended into 400 ml of water and the slurry pH is adjusted to 8.5 with 1 Molar sodium hydroxide. Over a period of two days, the pH is periodically checked and adjusted to 8.5 with sodium hydroxide. During this period, the fibers exchange to the sodium salt form, which is highly absorbent. Thus, the fibers swell up. The fully swollen fibers of the invention are collected by suction filtration and are washed with distilled water. Their wet weight is 460.0 g and their consistency is determined to be 1.40 %, from which the Fiber Yield is calculated to be 6.44 g of fiber of the invention. The Conversion is about 94 %. The WAARV of the fiber of this Example is determined as 53.9 g/g.

EXAMPLE III

Preparation of fiber of the invention.

GANTREZ S-97 (2.23 g) is dissolved by adding it portionwise to 15 ml of water while stirring and heating to 65–70° C. To the solution is added polyethylene glycol (0.333 g, nominal molecular weight 3350) predissolved in 5 ml of water. Stirring is continued until dissolution is complete. The resulting aqueous medium is now cooled to ambient temperature and the pH is adjusted to 3.00 with 1 Molar sodium hydroxide. Loose fibers chemithermomechanical pulp (2.00 g) are added. The resulting slurry is thoroughly mixed and is spread out into a thin layer on a piece of aluminum foil. The slurry layer is dried in an oven at 65–70° C., a temperature selected to minimize or avoid crosslinking reactions. The layer, now about 1 mm thick, is removed from the foil and cured by placing it in an oven preheated to a curing temperature of 130° C. The curing time is 5.0 minutes. The layer is cooled to ambient temperature. This yields raw fiber in the acid form, which is not particularly absorbent. The fiber is then repulped. In practice it is convenient to break it into small pieces and add it to 400 ml of distilled water. After further stirring (e.g., 1 hour) the pH of the mixture is adjusted to 2.0 with hydrochloric acid and it is mixed in a Waring Blendor for 1 minute on low speed. The fibers, still in the acid form, are collected by suction filtration in a Buchner funnel fitted with a handsheet forming wire, washed with 500 ml of water, and are re-suspended into 500 ml of water. The slurry pH is adjusted to 8.5 using 1 Molar sodium hydroxide in water. (Using potassium hydroxide or lithium hydroxide instead of sodium hydroxide at this stage would result in the potassium or lithium form of the fibers.) Over one day, the pH is periodically checked and readjusted to 8.5 with sodium hydroxide. During this period, the fibers exchange to the sodium salt form, which is highly absorbent. Thus, the fibers swell up. The fully swollen fibers of the invention are collected by suction filtration and are washed with distilled water. Their wet weight is 238 g and their consistency is determined to be 1.53 %, from which the Fiber Yield is calculated to be 3.63 g of fiber of the invention. The Conversion is about 80%. The WAARV of the fiber of this Example is determined as 52.6 g/g.

EXAMPLES IV–XI

The procedure of Example III is repeated except that the cellulosic starting-material fiber is as indicated in the following table.

| Example | Cellulosic Fiber Type* | Conversion | WAARV (g/g) |
| --- | --- | --- | --- |
| IV | SSK | 91% | 37.1 |
| V | NSK | 94% | 28.3 |
| VI | Aspen | 99% | 34.2 |
| VII | Eucalyptus | 96% | 42.1 |
| VIII | Sulfite | 90% | 30.7 |
| IX | Cotton Linters | 87% | 38.7 |
| X | V-60 | 93% | 50.9 |
| XI | V-5 | 92% | 49.5 |

*These fibers are each identified in detail under the caption "Starting-materials" in the Experimental preamble supra.

EXAMPLE XII

The procedure of Example III is repeated except that the curing time is 4.0 minutes at a curing temperature of 130° C. The procedure yields fibers having a wet weight of 246 g and a consistency of 1.15 % from which the Fiber Yield is calculated to be about 2.83 g. The Conversion is about 62 %. The WAARV of the fiber of this Example is determined to be 65.9 g/g.

EXAMPLE XIII

The procedure of Example III is repeated except that the curing time is 4.5 minutes at a curing temperature of 130° C. The procedure yields fibers having a wet weight of 219 g and a consistency of 1.80 % from which the Fiber Yield is calculated to be about 3.95 g. The Conversion is about 87 %. The WAARV of the fiber of this Example is determined to be 46.2 g/g.

EXAMPLE XIV

The procedure of Example III is repeated except that the curing time is 6.5 minutes at a curing temperature of 130° C. The procedure yields fibers having a wet weight of 106 g and a consistency of 4.10 % from which the Fiber Yield is calculated to be about 4.34 g. The Conversion is about 95 %. The WAARV of the fiber of this Example is determined to be 16.1 g/g.

EXAMPLE XV

The procedure of Example III is repeated except that the pH of the aqueous medium is 1.75 and the curing time is 6.5 minutes at a curing temperature of 130° C. The procedure yields fibers having a wet weight of 171 g and a consistency of 2.24 % from which the Fiber Yield is calculated to be about 3.83 g. The Conversion is about 84 %. The WAARV of the fiber of this Example is determined to be 34.4 g/g.

EXAMPLE XVI

The procedure of Example III is repeated except that the pH of the aqueous medium is 2.00 and the curing time is 6.5 minutes at a curing temperature of 130° C. The procedure yields fibers having a wet weight of 139 g and a consistency of 2.83 % from which the Fiber Yield is calculated to be about 3.93 g. The Conversion is about 86%. The WAARV of the fiber of this Example is determined to be 27.8 g/g.

EXAMPLE XVII

The procedure of Example I is repeated except that polyethylene glycol with a nominal molecular weight of 200 (0.150 g) is used in place of PEG 3350. The procedure yields fibers having a wet weight of 333 g and a consistency of 1.51 % from which the Fiber Yield is calculated to be about 5.04 g. The Conversion about 78%. The WAARV of the fiber of this Example is determined to be 51.4 g/g.

EXAMPLE XVIII

The procedure of Example I is repeated except that polyethylene glycol with a nominal molecular weight of 600 (0.225 g) is used. The procedure yields fibers having a wet weight of 294 g and a consistency of 1.88% from which the Fiber Yield is calculated to be about 5.53 g. The Conversion is about 84%. The WAARV of the fiber of this Example is determined to be 41.7 g/g.

EXAMPLE XIX

The procedure of Example I is repeated except that polyethylene glycol with a nominal molecular weight of 1,000 (0.360 g) is used. The procedure yields fibers having a wet weight of 253 g and a consistency of 2.24% from which the Fiber Yield is calculated to be about 5.67 g. The Conversion is about 85 %. The WAARV of the fiber of this Example is determined to be 33.8 g/g.

EXAMPLE XX

The procedure of Example I is repeated except that polyethylene glycol with a nominal molecular weight of 6,800 (0.750 g) is used. The procedure yields fibers having a wet weight of 259 g and a consistency of 2.51% from which the Fiber Yield is calculated to be about 6.50 g. The conversion is about 92 %. The WAARV of the fiber of this Example is determined to be 36.0 g/g.

EXAMPLE XXI

The procedure of Example III is repeated with the following exceptions: the pH of the aqueous medium is 1.60 and the curing time is 29.1 minutes at a curing temperature of 115° C. The procedure yields fibers having a wet weight of 220 g and a consistency of 1.86 % from which the Fiber Yield is calculated to be about 4.09 g. The Conversion is about 90 %. The WAARV of the fiber of this Example is determined to be 46.2 g/g.

EXAMPLE XXII

The procedure of Example III is repeated with the following exceptions: the pH of the aqueous medium is 1.60 and the curing time is 16.5 minutes at a curing temperature of 120° C. The procedure yields fibers having a wet weight of 240 g and a consistency of 1.52 % from which the Fiber Yield is calculated to be about 3.65 g. The Conversion is about 80%. The WAARV of the fiber of this Example is determined to be 55.2 g/g.

EXAMPLE XXIII

The procedure of Example XXI is repeated with the following exceptions: the pH of the aqueous medium is 1.60 and the curing time is 4.5 minutes at a curing temperature of 135° C. The procedure yields fibers having a wet weight of 231 g and a consistency of 1.29% from which the Fiber Yield is calculated to be about 2.97 g. The Conversion is about 65 %. The WAARV of the fiber of this Example is determined to be 66.5 g/g.

EXAMPLE XXIV

Preparation of a wet-laid paper comprising fiber of the invention (Example I) in admixture with conventional fiber.

A slurry of northern softwood Kraft pulp is prepared by repulping NSK dry-lap (1.75 g bone-dry basis) in 400 ml of distilled water in a Waring Blendor on low speed for 1.0 minute. The slurry is placed in a 1 liter beaker and to it is added fiber of the invention (sodium form, made according to Example I but never dried, 0.75 g bone-dry basis, in 100 ml of distilled water). The pH of the slurry is adjusted to 8.5 with 0.1 Molar sodium hydroxide and the slurry is stirred for 1 hour. The deckle box is fitted with a forming wire (Albany International-Appelton Wire Division, Appelton, Wis.; Hadsheet style/mesh 78-S) and is filled with distilled water which is also adjusted to pH 8.5 with 1 Molar sodium hydroxide. The slurry is added and the water is drained by suction. The wet paper sheet (handsheet) thus formed is transferred to a drying fabric (Albany International-Appelton Wire Division, Appelton, Wis.; Handsheet style/mesh 36-C) by passage over a vacuum slit on low setting. The drying fabric is passed over the vacuum slit two additional times on high setting and then another fabric is placed on top of the wet handsheet. The sandwich is passed through a drum dryer at 230° F. until the sheet is dry. This gives a 2.50 g handsheet (basis weight=16.5 pounds/3,000 square feet) containing 30% by weight of the fiber of the invention. This handsheet is quick-wicking and has a WAARV of 14.0 g/g. The handsheet can be wetted and re-dried; on rewet, it is found to have preserved good absorbency and wicking characteristics.

EXAMPLE XXV

Preparation of a wet-laid paper comprising fiber of the invention (Example II) in admixture with conventional fiber.

The procedure of Example XXIV is repeated except that the fiber of the invention of Example II is used. The WAARV of the handsheet is determined to be 14.2 g/g.

EXAMPLE XXVI

Preparation of a wet-laid paper comprising fiber of the invention (Example III) in admixture with conventional fiber.

The procedure of Example XXIV is repeated except that the fiber of the invention of Example III is used. The WAARV of the handsheet is determined to be 12.6 g/g.

EXAMPLE XXVII

Preparation of a wet-laid paper comprising fiber of the invention (Example IV) in admixture with conventional fiber.

The procedure of Example XXIV is repeated except that the fiber of the invention of Example IV is used. The WAARV of the handsheet is determined to be 8.8 g/g.

EXAMPLE XXVIII

Preparation of a wet-laid paper comprising fiber of the invention (Example V) in admixture with conventional fiber.

The procedure of Example XXIV is repeated except that the fiber of the invention of Example V is used. The WAARV of the handsheet is determined to be 8.2 g/g.

EXAMPLE XXIX

Preparation of a wet-laid paper comprising fiber of the invention (Example VI) in admixture with conventional fiber.

The procedure of Example XXIV is repeated except that the fiber of the invention of Example VI is used. The WAARV of the handsheet is determined to be 6.3 g/g.

EXAMPLE XXX

Preparation of a wet-laid paper comprising fiber of the invention (Example VII) in admixture with conventional fiber.

The procedure of Example XXIV is repeated except that the fiber of the invention of Example VII is used. The WAARV of the handsheet is determined to be 8.5 g/g.

EXAMPLE XXXI

Preparation of a wet-laid paper comprising fiber of the invention (Example VIII) in admixture with conventional fiber.

The procedure of Example XXIV is repeated except that the fiber of the invention of Example VIII is used. The WAARV of the handsheet is determined to be 8.5 g/g.

XXXII

Preparation of a wet-laid paper comprising fiber of the invention (Example IX) in admixture with conventional fiber.

The procedure of Example XXIV is repeated except that the fiber of the invention of Example IX is used. The WAARV of the handsheet is determined to be 10.5 g/g.

EXAMPLE XXXIII

Preparation of a wet-laid paper comprising fiber of the invention (Example X) in admixture with conventional fiber.

The procedure of Example XXIV is repeated except that the fiber of the invention of Example X is used. The WAARV of the handsheet is determined to be 8.8 g/g.

EXAMPLE XXXIV

Preparation of a wet-laid paper comprising fiber of the invention (Example XI) in admixture with conventional fiber.

The procedure of Example XXIV is repeated except that the fiber of the invention of Example XI is used. The WAARV of the handsheet is determined to be 10.1 g/g.

EXAMPLES XXXV–XLVI

The procedure of Example XXIV is repeated except that the fiber of the invention of Examples XII–XXIII are used. The WAARV of the corresponding handsheets are given in the table below.

| Example | Fiber of the Invention | WAARV of Handsheet (g/g) |
|---------|------------------------|--------------------------|
| XXXV    | Example XII            | 9.4  |
| XXXVI   | Example XIII           | 7.4  |
| XXXVII  | Example XIV            | 6.1  |
| XXXVIII | Example XV             | 7.9  |
| XXXIX   | Example XVI            | 8.4  |
| XL      | Example XVII           | 13.6 |
| XLI     | Example XVIII          | 12.3 |
| XLIII   | Example XIX            | 9.0  |
| XLIV    | Example XX             | 13.2 |
| XLV     | Example XXI            | 10.9 |
| XLVI    | Example XXII           | 11.7 |
| XLVII   | Example XXIII          | 9.3  |

Test Methods pH of aqueous medium: pH in general

In general, pH herein is determined using a conventional digital pH meter which has an accuracy of ±0.01 pH units (Markson model 88). The meter is equipped with a flat surface electrode, which has a peripheral porous polyethylene junction (Markson 1208B). The electrode is particularly suited for measuring the pH of slurries, viscous solutions and wet surfaces. As an alternative, a conventional gel-filled, polymer body pH electrode may be used. pH measurements are made at ambient temperature, in the range 20° C.–25° C. The electrodes are calibrated in the conventional manner, using pH 7.00 and pH 4.00 buffers.

It is specifically noted that the above-identified equipment and procedure is used for measuring pH of the aqueous medium discussed hereinabove in the specification.

Consistency

Consistency, such as of wet fiber of the invention, is defined as percentage by weight of a specified fiber, in a slurry, fiber dispersion or wet fiber mass. Measurement is carried out by placing a sample of wet material sufficient to give at least about 0.1 gram of bone dry fiber on a Mettler PM460 balance which is equipped for moisture determination (infrared dryer model LP16), weighing wet followed by continuous monitoring of weight during drying (90° C. temperature setting) to constant weight.

Fiber Yield

Fiber Yield is defined as the weight in grams, dry basis, of fiber of the invention, sodium form. It is conveniently measured by multiplying the weight of wet, swollen fibers, by the consistency.

Conversion

Conversion is defined as the yield of fiber of the invention expressed in percentage terms. It is calculated by dividing the Fiber Yield by the sum of weights of starting-materials, more specifically the sum of weights, bone dry basis, of poly(methyl vinyl ether-co-maleate) copolymer plus polyol plus cellulosic fiber starting-material.

In determining Conversion, the weight of poly(methyl vinyl ether-co-maleate) in the above is expressed on an acid equivalent basis. That is to say, regardless of the form of the poly(methyl vinyl ether-co-maleate) copolymer used in the synthesis of the fiber of the invention, and equally regardless of the form of the product fiber, the convention is adopted of everywhere specifying the poly(methyl vinyl ether-co-maleate) copolymer weight as though it were in the acid form. In this manner, the relative proportion of poly(methyl vinyl ether-co-maleate) copolymer to the cellulose and polyol components is unambiguously determined.

Water absorbency and retention value (WAARV) of fiber of the invention and WAARV of wet-laid paper containing same:

The following is a gravimetric water-absorbency and retention-measuring method applicable to characterizing the fibers, pulps or paper webs according to the invention. For purposes of comparison, typical papermaking pulp such as Kraft pulp measures of the order of about 3–4 grams of water per gram of fiber at pH 8.5 ("g/g") by this method and paper webs made from such pulp have similar or slightly lower values. Equipment is as follows:

Sample holders: glass cylinders open at both ends, 1.8 cm. inside diameter, 4.2 cm height.

Tea-bag material: Tea-bag paper, grade 1234T, obtainable from C.H Dexter Division of the Dexter Corp., Windsor Locks, Conn. This paper is cut into 4.7×9.5 cm rectangles. The purpose of the tea-bag material is to provide a substantially non-absorbent pulp-retaining material through which water will pass during centrifugation, and which acts to prevent the possibility of obtaining artificially high pulp absorbencies, which might otherwise occur, e.g., if the pulp were allowed to block the constriction in the centrifuge tube.

Balance: 0.0001 g sensitivity.

Centrifuge: clinical model, variable speed, with a swinging bucket rotor, four 29.4 mm. inside diameter×95 mm depth shields, and tachometer adapted to measure centrifuge speed.

Centrifuge tubes: designed with a constriction so that on centrifuging, the water will separate into the lower half of the tube, leaving the sample and "teabag" in the upper half.

Drying beakers: 10 ml capacity.

Vacuum oven: capable of approximately 250 mTorr vacuum, heating to at least 110° C.; temperature thermostatted at 60° C.

Convection oven: thermostatted at 105° C.

Soaking beakers: 150 ml capacity.

For each absorbency determination, a number of replicated measurements (typically 2 will suffice provided that the results are in good agreement) are made, each based on the following procedure:

Weigh a tea-bag paper. The weight is the Initial Teabag Weight (Initial Teabag Weight=ITB) and is typically of the order of 70 mg.

Place the fiber or paper (shredded in small pieces) which is to be tested for absorbency into a 150 ml beaker. Add 100 ml distilled water. Adjust pH to 8.5 with aqueous sodium hydroxide. Equilibrate by allowing to stand for about 2 hours.

Fold a weighed tea-bag paper to make a cylindrically shaped holder having one end closed and the other end open. Place it inside a glass cylinder. Into the shaped tea-bag, place wet equilibrated material to be tested, allowing excess water to drain through the tea-bag, until the tea-bag is substantially full with wet fiber.

(Typically when the sample to be tested is fiber of the invention, the sample size is sufficient to contain about 100 mg bone dry fiber; when the sample to be tested is a wet-laid paper containing the fiber of the invention, the sample size is sufficient to contain about 300 mg in total of all fiber present; and when the sample to be tested is conventional fiber, e.g., northern softwood Kraft, the sample size is sufficient to contain about 500 mg of fiber. Slip the tea-bag out of the glass cylinder or holder and, preserving the cylindrical shape of the tea-bag, place it and its sample contents in a centrifuge tube. Centrifuge at approximately 125 "g" (gravities) force for 10 minutes, centrifuge speed-up time not included. Place the centrifuged sample and tea-bag in an accurately preweighed dry beaker (dry beaker weight =DBW). Weigh the centrifuged sample, tea-bag and beaker (weight =$W_1$). Dry in the 105° C. convection oven for 3 hours. Further dry in the vacuum oven for 6 hours or more. Allow to cool in a desiccator. Weigh (weight=$W_2$). The water absorbency and retention value (WAARV) of the sample (g/g) is given by the following formula:

$$WAARV = (WPW - DPW)/DPW$$

wherein
WPW=wet pulp weight=$W_1$−(ITB+DBW) and
DPW=dry pulp weight=$W_2$ −(ITB+DBW).

In principle, it is possible to measure WAARV absorbency at pH values other than 8.5 of the above-specified method. However, unless there is a specific mention of another pH, any WAARV absorbency value quoted throughout the instant specification and claims, expressed simply in g/g, is strictly to be construed as a measurement at a pH of 8.5.

What is claimed is:

1. A chemically modified fiber having a water absorbency and retention value in the range of from about 15 g/g to about 100 g/g comprising, chemically bonded together:

(a) a cellulosic fiber selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleach softwood sulfite pulp fiber, bleached hardwood sulfite pulp fiber, unbleached softwood sulfite pulp fiber, unbleached hardwood sulfite pulp fiber, cotton linters, mercerized dissolving pulp fiber, unmercerized dissolving pulp fiber, and mixtures thereof;

(b) a poly(methyl vinyl ether-co-maleate) 1:1 copolymer having a number average molecular weight in the range of from about 39,000 to about 80,000, and (c) a polyol selected from the group consisting of polyvinyl alcohol, propylene glycol, glycerin, pentaerythritol, a diol having the formula $HO(CH_2CH_2O)_nH$, wherein n is from 1 to about 154;

wherein the proportion by weight of said poly(methyl vinyl ether-co-maleate) copolymer to said polyol is from about 250:1 to about 3:1 and the weight of said poly(methyl vinyl ether-co-maleate) copolymer plus said polyol per unit weight of said cellulosic fiber, (a), is in the range from about 0.3 to about 2, the poly(methyl vinyl ether-co-maleate) copolymer weight being expressed on an acid equivalent basis.

2. A chemically modified fiber according to claim 1 wherein said cellulosic fiber, (a), is selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber and mixtures thereof; said poly(methyl vinyl ether-co-maleate) copolymer has number average molecular weight in the range from about 41,000 to about 80,000; and said polyol is a diol.

3. A chemically modified fiber according to claim 2 wherein said polyol is selected from the group consisting of diols of formula $HO(CH_2CH_2O)_nH$ wherein n is from about 4 to about 154; and said proportion by weight of poly(methyl vinyl ether-co-maleate) copolymer to polyol is from about 30:1 to about 4:1.

4. A chemically modified fiber according to claim 3 wherein said poly(methyl vinyl ether-co-maleate) copolymer has number average molecular weight in the range from about 67,000 to about 80,000; n in said formula is from about 34 to about 100; and said weight of poly(methyl vinyl ether-co-maleate) copolymer plus polyol per unit weight of said cellulosic fiber, (a), is in the range from about 0.6 to about 1.5.

5. A chemically modified fiber according to claim 4 wherein said water absorbency and retention value is in the range from about 25 g/g to about 90 g/g.

6. A chemically modified fiber according to claim 5 wherein n in said formula is from about 70 to about 80; said proportion by weight of poly(methyl vinyl ether-co-maleate) copolymer to polyol is from about 10:1 to about 5:1; and said weight of poly(methyl vinyl ether-co-maleate) copolymer plus polyol per unit weight of cellulosic fiber, (a), is in the range from about 0.8 to about 1.2.

7. A chemically modified fiber according to claim 6 wherein said water absorbency and retention value is in the range from about 50 g/g to about 80 g/g.

8. A chemically modified fiber according to claim 7 wherein the cations, which are inherently present in a charge-balancing amount, are selected from the group consisting of sodium, potassium, lithium, hydrogen and mixtures thereof.

9. A chemically modified fiber according to claim 8 wherein said cations are selected from the group consisting of sodium, hydrogen and mixtures thereof.

10. A cellulosic papermaking pulp consisting essentially of the chemically modified fiber of claim 1.

11. A cellulosic papermaking pulp consisting essentially of the chemically modified fiber of claim 9.

12. A cellulosic papermaking pulp according to claim 11 wherein the content of cations which are hydrogen is such as to produce a pH of less than 5 when dispersed in water.

13. A cellulosic papermaking pulp according to claim 11 wherein the content of cations which are hydrogen is such as to produce a pH of about 6 to about 9 when dispersed in water.

14. A cellulosic papermaking pulp consisting essentially of: from about 5% to about 60% of the chemically modified fibers of claim 11 and from about 40% to about 95% of conventional cellulosic fiber.

15. A process for preparing a chemically modified fiber having a water absorbency and retention value in the range of from about 15 g/g to about 100 g/g comprising a step of:

thermally cross-linking, at a curing temperature of from about 100° C. to about 140° C. for a curing time of from about 120 minutes to about 3 minutes, (a) a starting-material pulp consisting essentially of cellulosic fiber selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood sulfite pulp fiber, unbleached softwood sulfite pulp fiber, cotton linters, mercerized dissolving pulp fiber, unmercerized dissolving pulp fiber, and mixtures thereof; with an intimate mixture of: (b) a poly(methyl vinyl ether-co-maleate) copolymer having a nominal number average molecular weight in the general range of from about 39,000 to about 80,000, and (c) a polyol selected from the group consisting of polyvinyl alcohol, propylene glycol, glycerin, pentaerythritol, a diol having the formula $HO(CH_2CH_2O)_nH$, wherein n is from 1 to about 154, wherein the proportion by weight of poly(methyl vinyl ether-co-maleate) copolymer to polyol is from about 250:1 to about 3:1 and the weight of poly(methyl vinyl ether-co-maleate) copolymer plus polyol per unit weight of cellulosic fiber, (a), is in the range from about 0.3 to about 2, wherein the poly(methyl vinyl ether-co-maleate) copolymer weight is expressed on an acid equivalent basis.

16. A process according to claim 15 comprising a step of:

thermally crosslinking, at a curing temperature of from about 110° C. to about 135° C. for a curing time of from about 45 minutes to about 4 minutes, (a) starting-material pulp consisting essentially of cellulosic fiber selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber and mixtures thereof; with an intimate mixture of: (b) poly(methyl vinyl ether-co-maleate) copolymer having a methyl vinyl ether content of about 50 mole % and a maleate content of about 50 mole %, and (c) a polyol of formula $HO(CH_2CH_2O)_nH$ wherein n is from about 4 to about 154; wherein the proportion by weight of poly(methyl vinyl ether-co-maleate) copolymer to polyol is from about 30:1 to about 4:1 and the weight of poly(methyl vinyl ether-co-maleate) copolymer plus polyol per unit weight of cellulosic fiber, (a), is in the range from about 0.6 to about 1.5.

17. A process according to claim 16 comprising the steps, in sequence, of forming said intimate mixture of copolymer and polyol by evaporating an aqueous medium having a pH of from about 1.6 to about 3.5 in the presence of said starting-material pulp; followed by thermally crosslinking at said curing temperature for said curing time.

18. A process according to claim 16 wherein said starting-material pulp, said copolymer and said polyol are thermally crosslinked as a thin layer.

19. A process according to claim 18 consisting of the sequence of said evaporating and thermal crosslinking steps, followed by an additional step, of acid repulping in water, followed by an additional, fiber-swelling step, comprising neutralizing with sodium hydroxide.

20. A process according to claim 19, wherein said starting-material pulp consists essentially of chemithermomechanical pulp fiber.

21. The product of a process according to claim 20, consisting essentially of a chemically modified fiber having a water absorbency and retention value in the range from about 25 g/g to about 90 g/g.

22. A process according to claim 19, wherein said starting-material pulp consists essentially of cellulosic fiber selected from the group consisting of bleached hardwood Kraft pulp fiber, bleached softwood Kraft pulp fiber, unbleached hardwood Kraft pulp fiber, unbleached softwood Kraft pulp fiber and mixtures thereof and the pH of said aqueous medium is from about 2.5 to about 3.5.

23. A process according to claim 19, wherein said starting-material pulp is chemithermomechanical pulp fiber, the pH of said aqueous medium is from about 1.6 to about 3.0, said curing temperature is from about 125° C. to about 130° C., and said curing time is from about 11 minutes to about 5 minutes.

24. The product of a process according to claim 23, consisting essentially of a chemically modified fiber having a water absorbency and retention value in the range from about 25 g/g to about 90 g/g.

25. A wet-laid paper web, comprising from about 5% to about 60% of chemically modified fiber according to claim 1.

26. A wet-laid paper web, comprising from about 10% to about 60% of chemically modified fiber according to claim 6.

27. A wet-laid paper web, comprising from about 20% to about 50% of the product of claim 19.

28. A disposable absorbent article comprising one or more plies of a wet-laid paper web according to claim 25.

29. A disposable absorbent article comprising one or more plies of a wet-laid paper web according to claim 26.

30. A disposable absorbent article comprising one or more plies of a wet-laid paper web according to claim 27.

* * * * *